(12) United States Patent
DiMauro

(10) Patent No.: US 7,509,171 B2
(45) Date of Patent: Mar. 24, 2009

(54) METHOD OF REMOVING DELETERIOUS CHARGED MOLECULES FROM BRAIN TISSUE

(75) Inventor: Thomas M. DiMauro, Southboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 208 days.

(21) Appl. No.: 11/115,424

(22) Filed: Apr. 27, 2005

(65) Prior Publication Data
US 2006/0247731 A1 Nov. 2, 2006

(51) Int. Cl.
*A61N 1/30* (2006.01)

(52) U.S. Cl. .......................................... 607/45

(58) Field of Classification Search .................. 607/45, 607/115–117, 135, 139; 600/544
See application file for complete search history.

(56) References Cited

U.S. PATENT DOCUMENTS

| | | | | |
|---|---|---|---|---|
| 4,503,863 A * | 3/1985 | Katims | ........................ | 600/554 |
| 6,001,088 A * | 12/1999 | Roberts et al. | ............... | 604/501 |
| 6,077,237 A * | 6/2000 | Campbell et al. | ............ | 600/587 |
| 6,591,138 B1 * | 7/2003 | Fischell et al. | ................ | 607/45 |
| 7,244,769 B2 * | 7/2007 | Epstein et al. | .............. | 514/654 |
| 2002/0123678 A1 * | 9/2002 | Lerner et al. | ................ | 600/378 |
| 2002/0183683 A1 * | 12/2002 | Lerner | .......................... | 604/20 |
| 2004/0210269 A1 * | 10/2004 | Shalev et al. | ................... | 607/45 |
| 2005/0065574 A1 * | 3/2005 | Rezai | ........................... | 607/45 |
| 2005/0159790 A1 * | 7/2005 | Shalev | .......................... | 607/45 |
| 2006/0106430 A1 * | 5/2006 | Fowler et al. | ................. | 607/45 |

OTHER PUBLICATIONS

Davalos, Stroke, Apr. 1997; 28: 708-710.*

* cited by examiner

*Primary Examiner*—Carl H Layno
*Assistant Examiner*—Eugene T Wu

(57) ABSTRACT

Methods and devices for removing cationic glutamate or anionic aluminum complexes from brain tissue by applying a voltage to the brain tissue.

9 Claims, 17 Drawing Sheets

METHOD OF REMOVING DELETERIOUS CHARGED MOLECULES FROM BRAIN TISSUE

BACKGROUND OF THE INVENTION

In Alzheimer's Disease (AD), the cleavage of beta amyloid protein precursor from the intracellular membrane often produces a protein AB-42 which is incompletely removed by normal clearance processes. Over time, this protein is deposited as a beta amyloid protein Aβ plaque within brain tissue, leading to the local destruction of neurons. The Aβ plaque deposition is also believed to provoke an inflammatory response by microglia and macrophages. These cells are believed to respond to the plaque deposition by releasing pro-inflammatory cytokines and reactive oxygen species (ROS). Although the inflammatory response may be provoked in an effort to clear the brain tissue of the detrimental plaque, it is now believed that this inflammation also injures local neuronal tissue, thereby exacerbating AD.

High levels of aluminum, copper, iron, and zinc have been found in the brains of AD patients. For example, Finefrock, *J. Am. Geriatr. Soc.*, 51, 1143-1148, (2003) reports the following concentrations:

| Metal | Total Amyloid Plaque (ug/g) | AD Neuropil (ug/g) | Control neuropil (ug/g) |
| --- | --- | --- | --- |
| Copper | 25 | 19 | 04 |
| Iron | 53 | 39 | 19 |
| Zinc | 69 | 51 | 23 |
| Aluminum | — | — | — |

It has been hypothesized by Finefrock, supra, that age-related dyshomeostasis and environmental accumulation are responsible for these high metal levels.

Furthermore, it is believed that these heavy metals play a critical role in the precipitation of BAP. It is known that BAP binds to these heavy metals and even has highly specific binding sites for copper. Accordingly, high levels of these heavy metals have been found in BAP plaques. Huang, *J. Nutrition*, 2000, May 130(5S Supp.) 1488S-92S).

Moreover, since both copper and iron are redox active, these metal-laden deposits act as catalysts for cell-free redox reactions that generate hydrogen peroxide and consequently highly toxic hydroxyl radical.

Accordingly, it is believed that higher-than-normal levels of heavy metals in the brain are deleterious because they not only promote the deposition of BAP plaques, a portion of them promote oxidative stress when deposited.

Aluminum is of particular concern. It has long been hypothesized that aluminum plays a critical role in the pathogenesis of AD, although this point has remained controversial. Nonetheless, according to Gupta, *Cell Mol. Life Sci.*, 2005 January 62(2) 143-58, the neurotoxic effects of aluminum are beyond any doubt. Moreover, it has further been reported that, once it has entered the brain, aluminum is fairly persistent. Yokel, *Toxicol. Sciences*, 64, 77-82 (2001) has hypothesized an aluminum half-life in the rat brain of about 150 days, and in the human brain of about 12 years. According to Yokel, supra, repeated aluminum exposure paired with aluminum persistence produces aluminum accumulation. Therefore, the neurotoxicity and the long-half life of aluminum have made it a potential therapeutic target for AD.

Because it has been proposed that these heavy metals are a key lynchpin in the progression of AD, there have been numerous attempts to remove these heavy metals from brain tissue. The use of chelating agents such as desferrioxamine (DFO) and clioquinol has been investigated, and it has been found that these agents are effective in removal. See Finefrock, *J. Am. Geriatr. Soc.*, 51, 1143-1148, (2003). Yokel, *Toxicol. Sciences*, 64, 77-82 (2001) has reported that significant reduction of aluminum accumulation and effective treatment of aluminum toxicity requires prolonged DFO therapy. However, it has also been found that these chelating agents have many drawbacks, including systemic toxicity, significant discomfort during application (intramuscular injection ten times a week for two years), and non-specificity of metallic removal.

SUMMARY OF THE INVENTION

The present inventors have appreciated that when aluminum is taken up in the brain, about 90% of it becomes complexed with citrates. Yokel, *Env. Health Persp.*, 110(Supp. 5), October 2002, 699-704. Aluminum citrate is the major aluminum species in the brain ECF, accounting for about 60% of such aluminum species. Nagasawa, *Toxicology Letters*, 155 (2005) 289-96. In addition, the aluminum citrate complex is formed through coordination binding of aluminum with the hydroxyl group and the two terminal carboxylates of citrate, this leaving a free carboxylate and leading to dissociation at physiological pH, and is expected to be extremely stable. Nagasawa, supra.

Moreover, in the pH range of about 6.9-7.4, about 89% of these aluminum citrate complexes are essentially in the form of either $Al_3(H_{-1}cta)_3OH^{-4}$ or $Al_3(H_{-1}cta)_3OH^{-2}$. Yokel, *Brain Research*, 930 (2002) 101-110. Because of each these complexes behave essentially as highly charged, low molecular weight anions, there is a substantial likelihood that these anionic complexes are highly mobile when placed under the influence of an electric field.

Moreover, the present inventors have further appreciated that the cribriform plate located above the nasal cavity is a highly porous bony ledge that provides a convective conduit for the flow of fluids between the brain CSF and the nasal mucosa.

Accordingly, the present inventors have developed an invention that takes advantage of the mobility of anionic aluminum citrate complexes under an electric field and the permeability of the cribriform plate, wherein an anode is placed in the nasal cavity and a voltage is applied. The resulting electric field draws the highly mobile anionic aluminum citrate complexes from the brain extracellular fluid (ECF) and cerebrospinal fluid (CSF) through the cribriform plate and into the nasal cavity, thereby removing the harmful aluminum species the brain.

Moreover, because each of the anode and cathode can be positioned outside the brain, the above-described therapy can be performed non-invasively. In addition to the safety aspects afforded by this procedure, its non-invasive nature affords an opportunity to repeat its practice on a frequent (perhaps, daily) basis.

Support for the concept of driving highly charged entities through the cribriform plate is found in Lerner, *J. Drug Targeting*, June 2004, 12(5) 273-280. Lerner sought to delivered octreotide (a molecule with a charge of +2 at pH 5) from the nasal cavity to the brain, and enhanced this delivery by electrophoretic means (also called "iontophoresis"). Lerner placed a silver anode having a octreotide reservoir at the top of the nasal cavity near the cribriform plate and placed a return cathode near the back of the head, and then applied a voltage therebetween to produce a current of about 3 mA through the brain. Lerner reported that the amount of octreotide delivered to the brain increased about 2-13 fold when enhanced by iontophoresis when compared to controls.

The passage of aluminum through the nasal cavity is reported in Yokel, *Env. Health Persp.*, 110(Supp. 5), October 2002, 699-704.

Therefore, in accordance with the present invention, there is provided a method of treating a patient having brain tissue and a nasal cavity, comprising the steps of:
  a) applying a voltage between an anode and a cathode in an amount sufficient to drive charged species from brain tissue.

DETAILED DESCRIPTION

Figure 13:
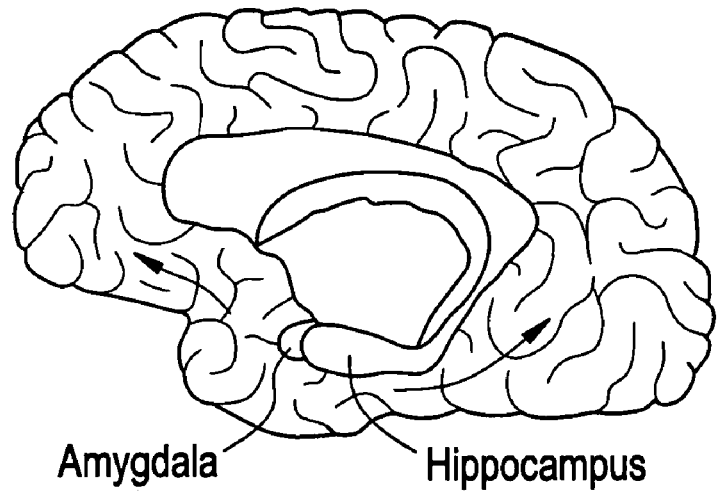
FIG. 13 is a saggital cross-section of the cerebrum of an Alzheimer's Disease (AD) patient showing the progression of the disease.

Now referring to FIG. 13, there is provided a saggital cross section of a brain afflicted with Alzheimer's Disease. In general, the disease often begins in the hippocampus, spreads to the amygdala, and proceeds anteriorly to the prefrontal cortex and posteriorly as well.

Figure 14:
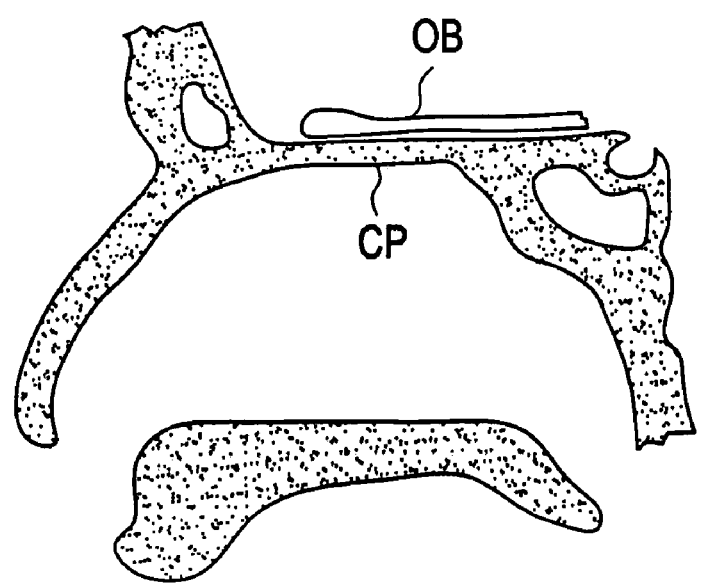
FIG. 14 is a saggital cross-section of a nasal septum and an olfactory bulb.

Now referring to FIG. 14, the cribriform plate CP is a wafer-thin ledge of porous bony tissue located beneath the prefrontal cortex portion of the brain and above the nasal cavity. The porosity of the cribriform plate is filled with olfactory nerves extending from the olfactory bulb OB (located at the lower base of the brain) and terminating within the nasal mucosa. As shown here, the cribriform plate has a thickness of about 1 mm while the olfactory bulb has a thickness of about 3 mm.

Figure 15:
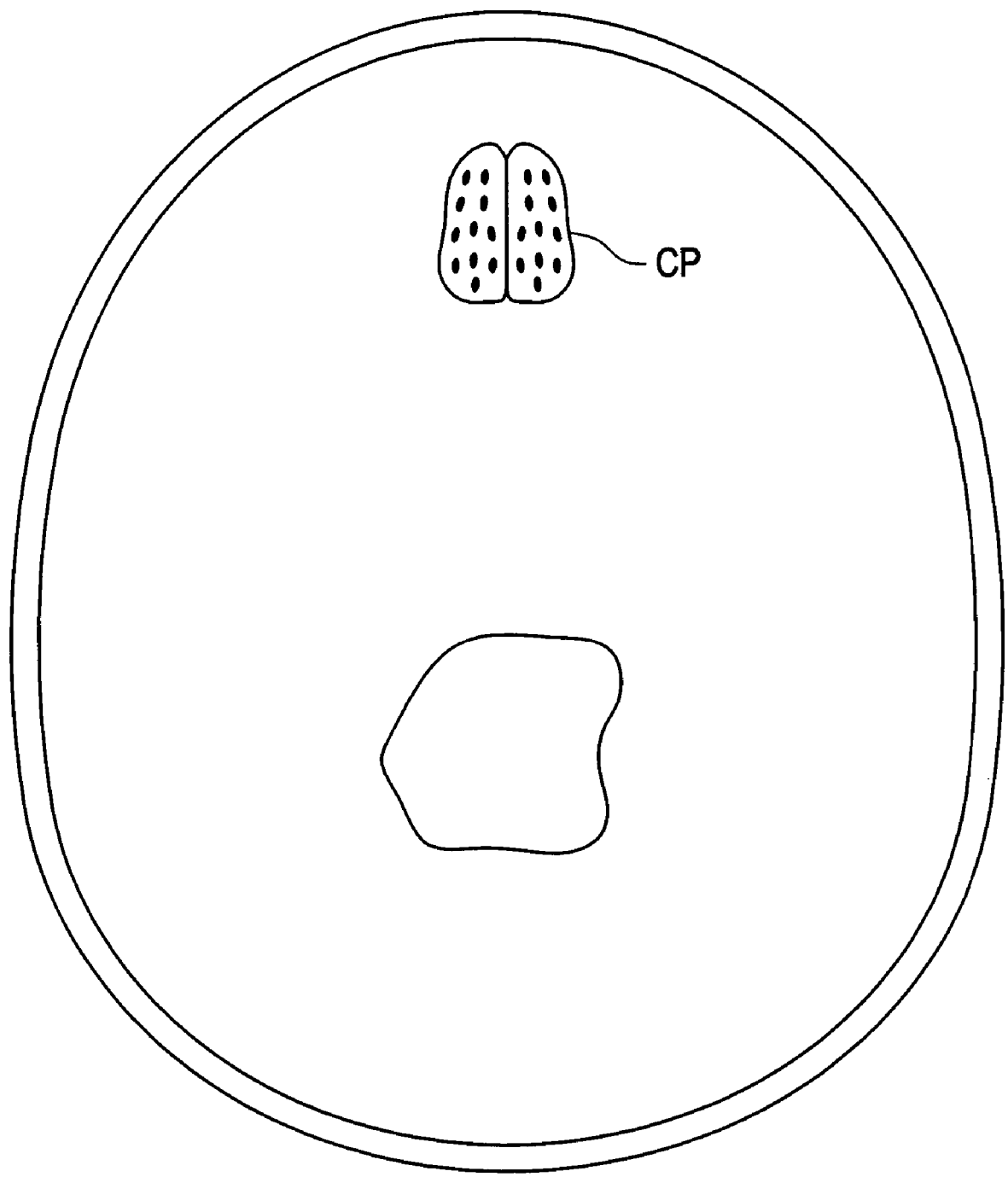
FIG. 15 is a coronal cross-section of a human skull.

Now referring to FIG. 15, the coronal view of the cribriform plate reveals that fairly large throughholes extend transversely through about one-half of the cribriform plate. These throughholes comprises about 50 areal % of the cribriform plate.

Figure 16:
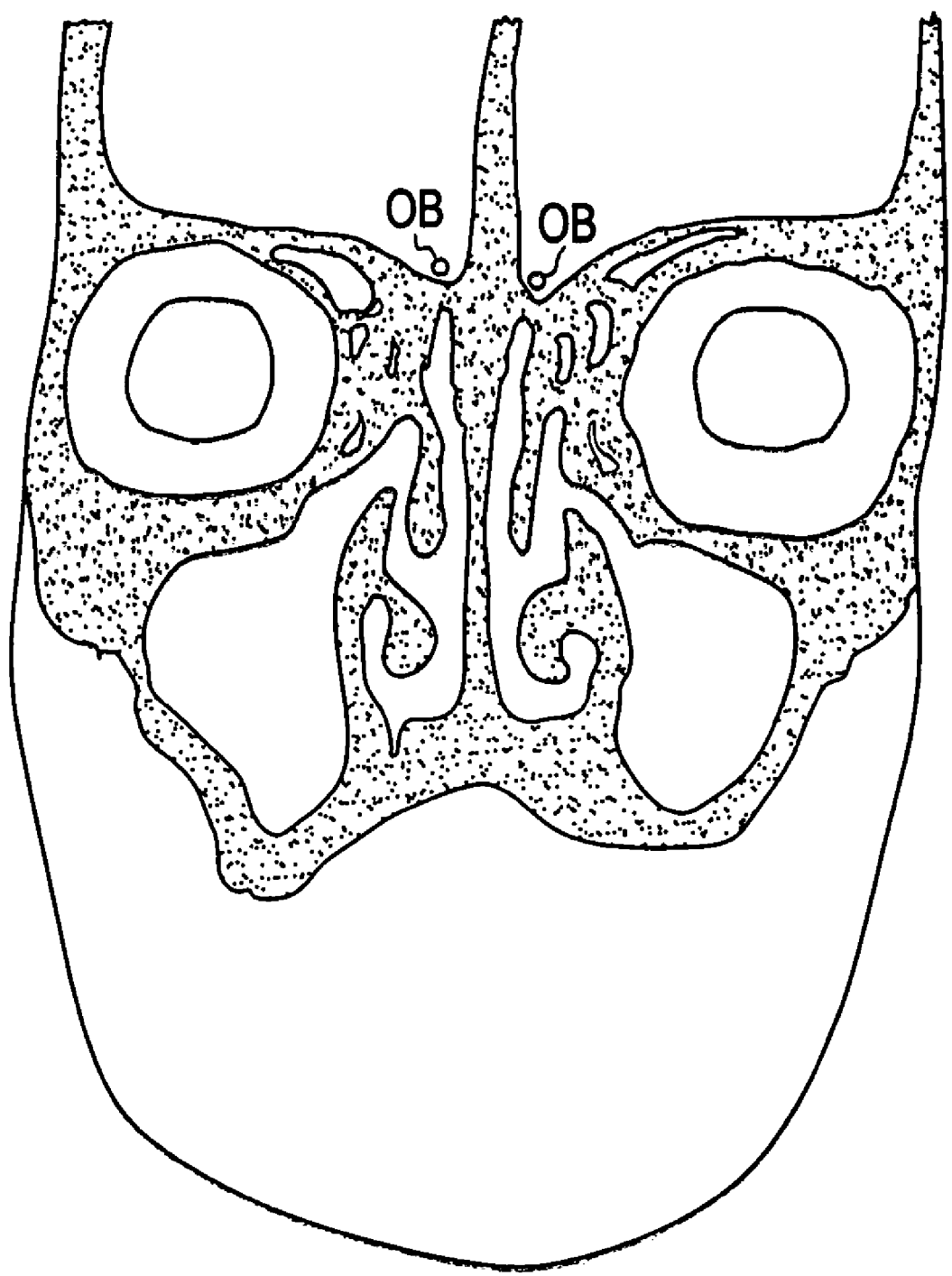
FIG. 16 is a frontal cross-section of a human skull.

Now referring to FIG. 16, this frontal cross-section shows that the thickness cribriform plate and the olfactory bulb comprise only about two mm.

Figure 1A:
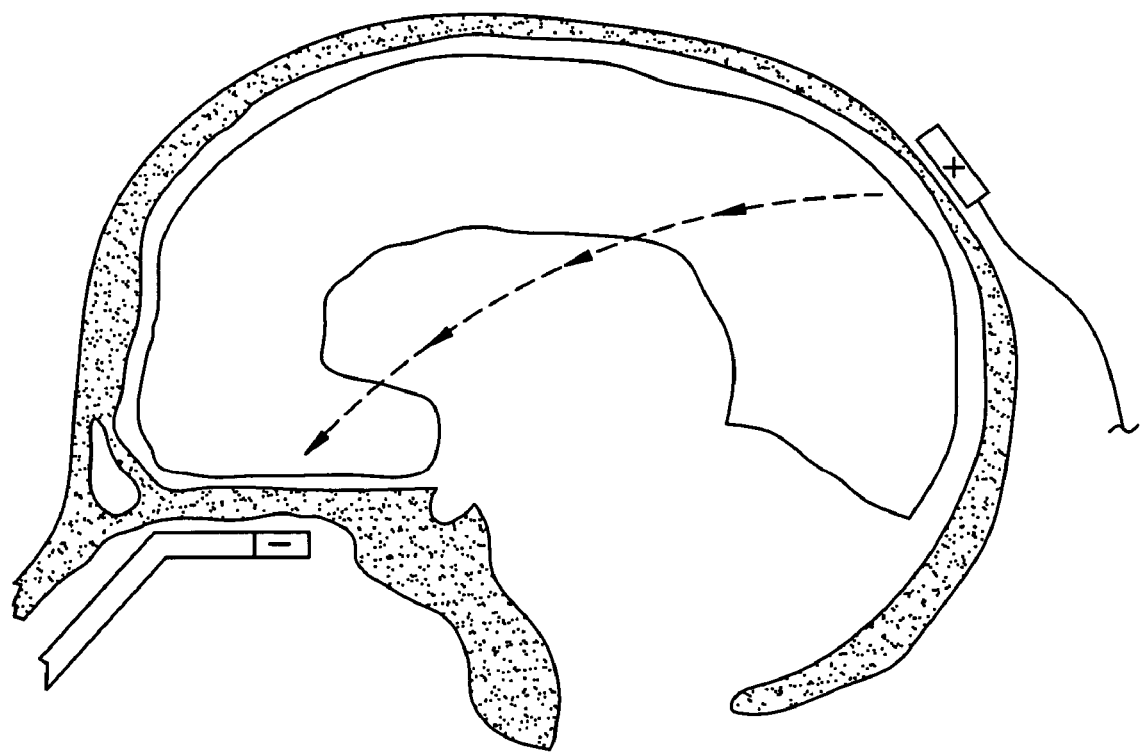
FIG. 1a is a cross-section of a cerebrum having an intranasal anode (−) and an occipital cathode (+).

Now referring to FIG. 1a, in some preferred embodiments, the anode is located in the nasal cavity and the cathode is located on the back of the skull. The resulting electric field draws the highly mobile anionic aluminum citrate complexes from the brain extracellular fluid (ECF) and cerebrospinal fluid (CSF) through the cribriform plate and into the nasal cavity, thereby removing the harmful aluminum from the brain.

Figure 1B:
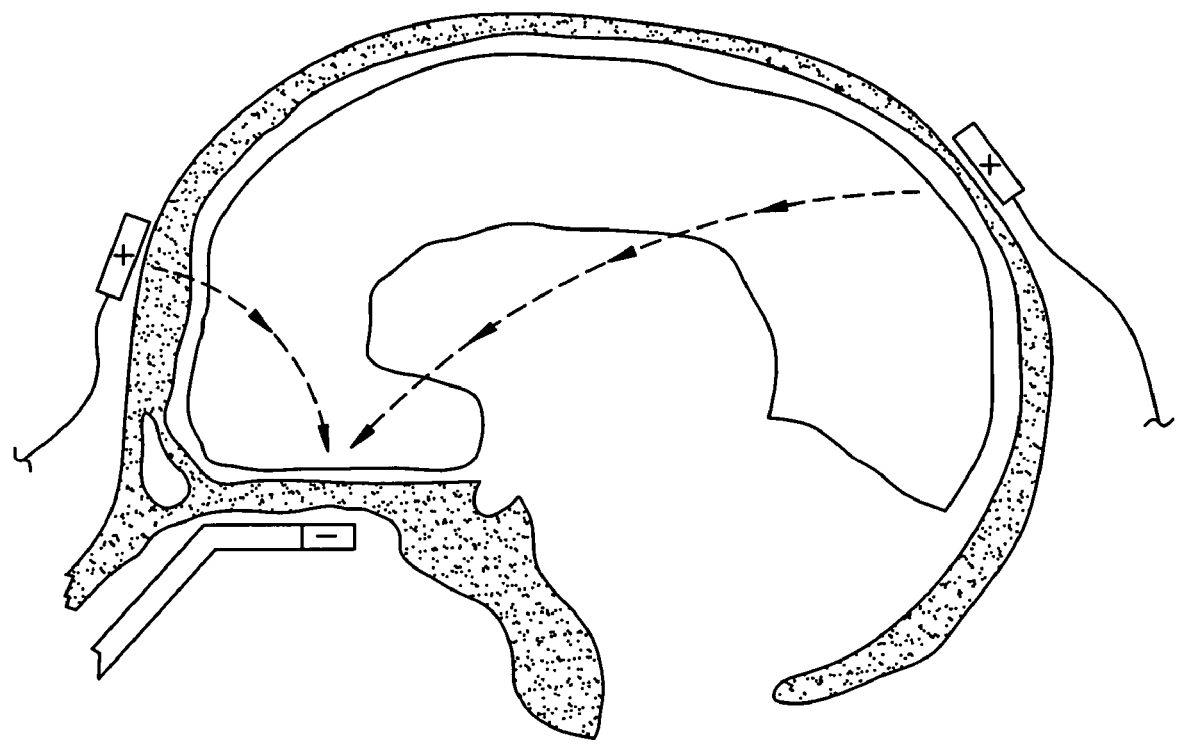
FIG. 1b is a cross-section of a cerebrum having an intranasal anode and a frontal and occipital cathode.

Now referring to FIG. 1b, in some preferred embodiments, the anode is located in the nasal cavity and the cathode is located on the forehead. The resulting electric field draws the highly mobile anionic aluminum citrate complexes from the frontal lobe's extracellular fluid (ECF) and cerebrospinal fluid (CSF) through the cribriform plate and into the nasal cavity, thereby removing the harmful aluminum from the frontal lobe.

In other preferred embodiments, cathodes are placed both upon the back of the skull and the forehead to draw aluminum species from both regions through the cribriform plate.

In preferred embodiments, the anode is placed near the top of the nasal cavity so that it abuts the cribiform plate. This abutment places the anode in electrical connection with the tissue of the olfactory bulb and therefore the brain.

Preferably, a pair of anodes are placed bilaterally in each half of the nasal cavity. However, in some embodiments, a single anode may be placed in a single half of the nasal cavity.

In some embodiments, the length of the anode spans at least one-quarter of the length of the cribriform plate. Because the length of the cribriform plate of the typical adult is at least about 2 cm, the length of the anode should be at least about 2 cm. More preferably, the length of the anode spans at least one-half of the length of the cribriform plate, more preferably substantially all of the cribriform plate. Full coverage of the cribriform plate is advantageous because it provides a larger cross-section through which the anion aluminum complex may pass, thereby offering a lower resistance path.

In some embodiments, the anode is surrounded by a conformable material that allows the anode to make good electrical connection with the nasal mucosa while avoiding damage to the nasal mucosa. In preferred embodiments thereof, the anode comprises a cotton wool portion. This cotton wool is advantageous because it not only conforms to the nasal mucosa abutting the cribriform plate, it also conforms to the lateral conchae, thereby providing a snug fit within the nasal cavity and preventing anode fallout.

The anode may be made from any conventional conductive material used in biomedical applications, including silver and copper. In some embodiments, the anode comprises magnesium. A magnesium anode possesses special advantage in that it will beneficially corrode and thereby provide magnesium ions to the brain tissue. It has been reported that magnesium ions impede the deposition of BAP.

Figure 2A:
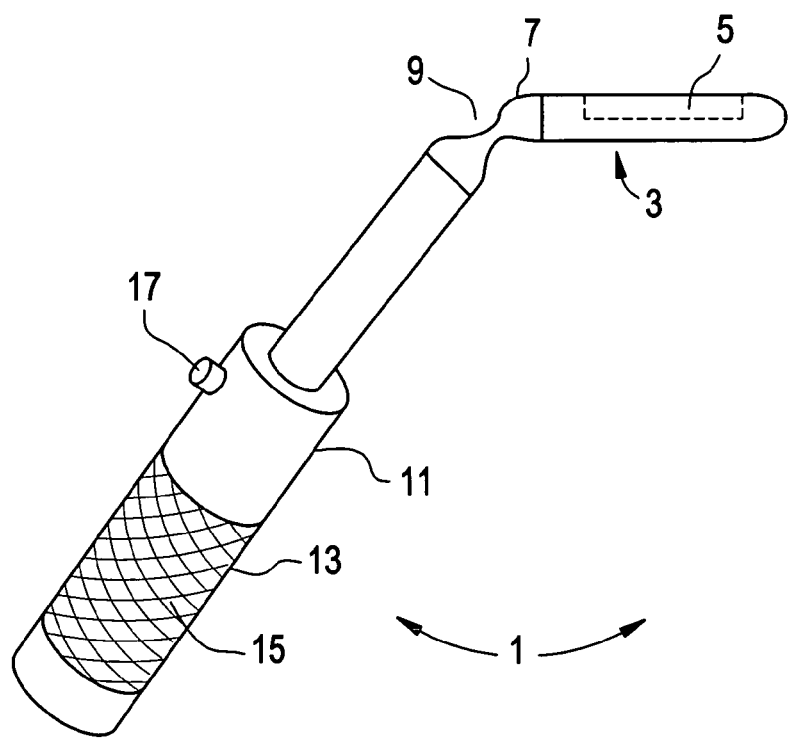
FIGS. 2a-2c disclose various views of a preferred intranasal electrode of the present invention.
Figure 2B:
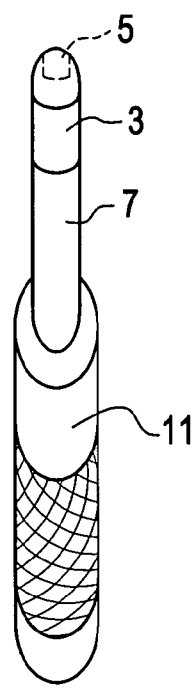
Figure 2C:
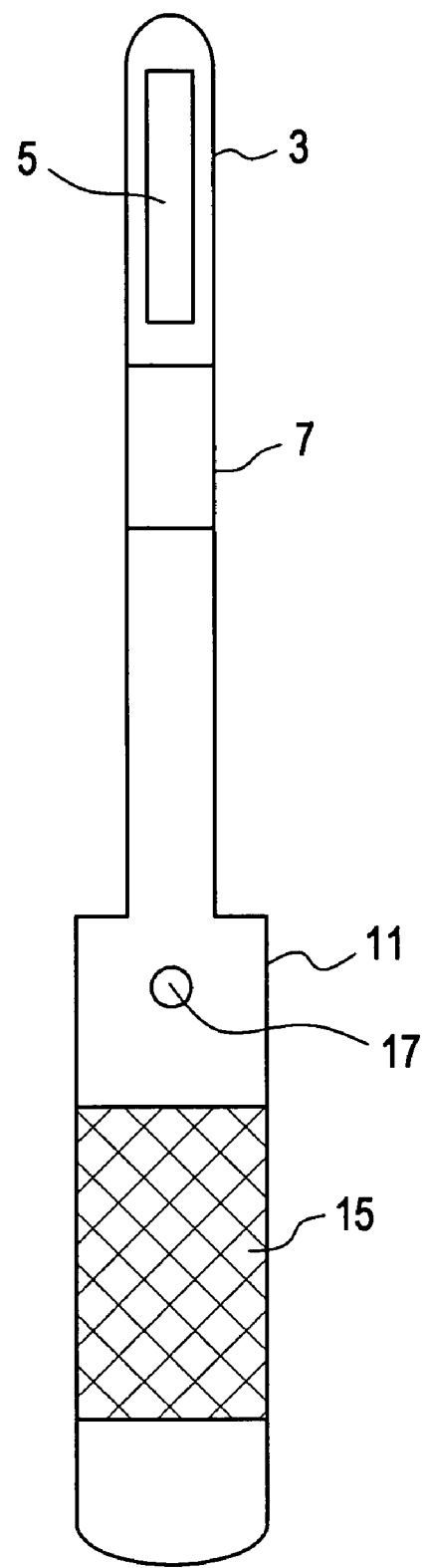

Now referring to FIGS. 2a-2c, there is provided a hand-held intranasal electrode probe 1 for treating a neurodegenerative disease in a patient, comprising:

a) a distal portion 3 adapted to fit within an upper portion of a nasal cavity and having an electrode 5 oriented towards the cribriform plate,
b) a flexible intermediate portion 7 having an angled, narrowed portion 9,
c) a proximal portion 11 having a handgrip 13 having a knurled surface 15 and an electrode activation button 17.

In some embodiments, the height of the distal portion is greater than its width. This allows its desired orientation within the thin regions of the nasal cavity.

In some embodiments, the distal portion is detachable from the remainder of the device. This allows it to be periodically cleaned by the user. In some embodiments, the tip of the distal portion is rounded in order to ease its entry into the nasal passage. In some embodiments, the length of the distal portion corresponds substantially to the length of the cribriform plate. This allows the anode to create an electric field substantially over the entire porosity of the cribriform plate. In some embodiments, the length of the anode corresponds substantially to the length of the cribriform plate. In some embodiments, the anode is oriented to face the cribriform plate upon insertion in the nasal passage. In some embodiments, the distal portion has an upper surface oriented to face the cribriform plate upon insertion.

Preferably, the cathode is placed so that an electric field is produced that causes anionic aluminum complexes to be drawn through the cribriform plate. In some embodiments, the cathode is attached to a separate probe and is attached to the back of the skull of the patient.

Figure 3:
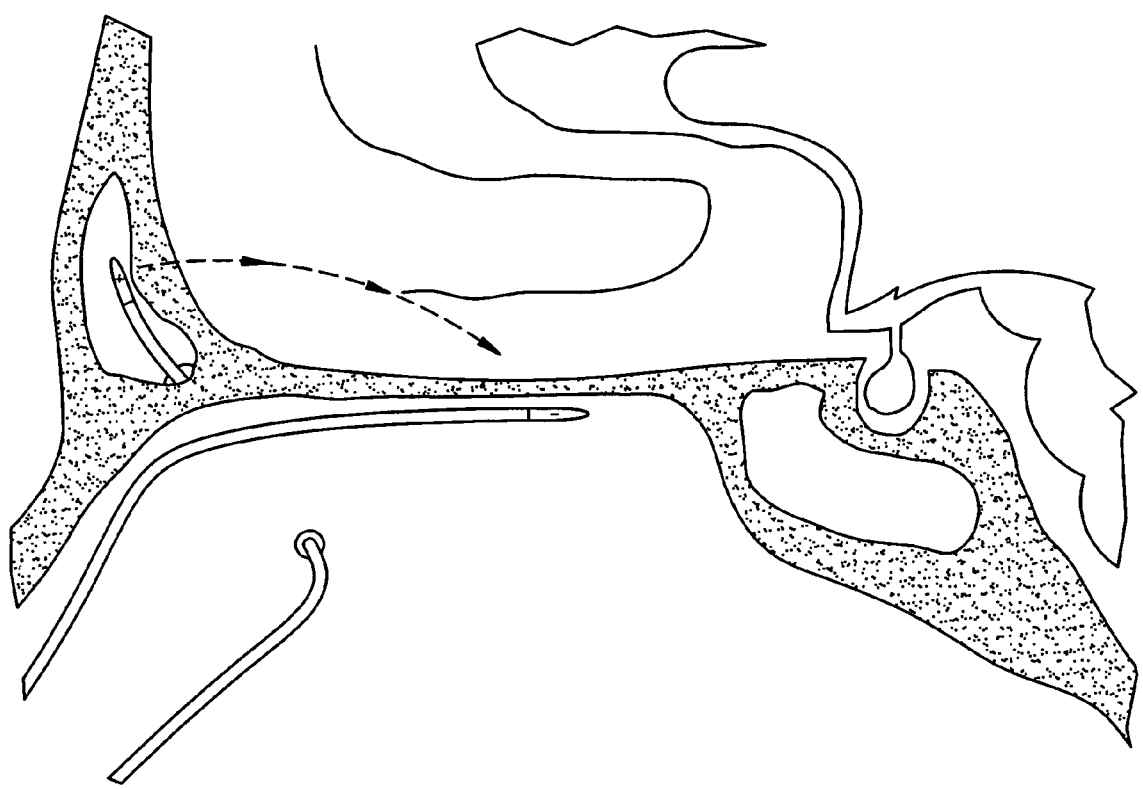
FIGS. 3-5 are saggital cross-sections of various electrode embodiments inserted into the nasal cavity and its surroundings.

Now referring to FIG. 3, in some embodiments, the cathode is placed in the frontal sinus. When combined with an anode situated near the cribriform plate and a voltage is applied, an electric field (shown as a dotted line) traversing the frontal portion of the prefrontal cortex is created. Accordingly, this embodiment allows specific removal of anionic aluminum complexes within the anterior portion of the prefrontal cortex.

Now referring to back to FIG. 1b, in some embodiments, the cathode is placed on the forehead of the patient. When combined with an anode situated near the cribriform plate and a voltage is applied, an electric field traversing the frontal lobe is created. Accordingly, this embodiment allows specific removal of anionic aluminum complexes within the frontal lobe.

Figure 4:
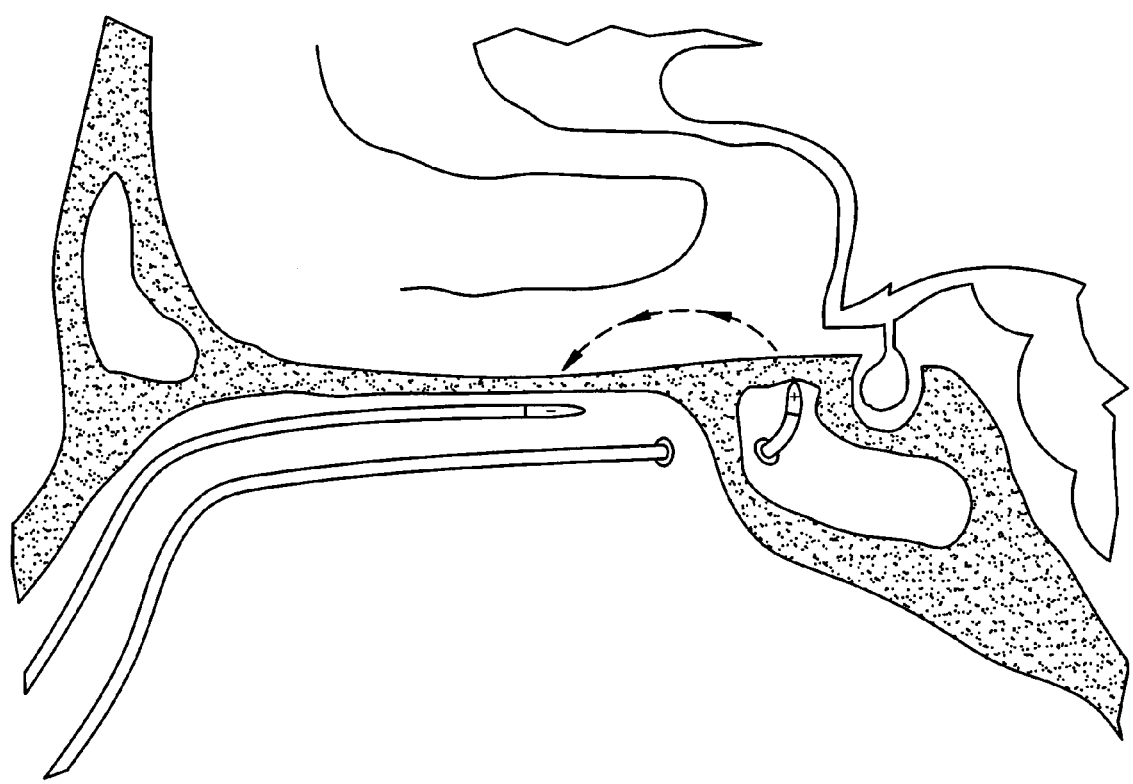

Now referring to back to FIG. 4, in some embodiments, the cathode is placed in the sphenoidal sinus. When combined with an anode situated near the cribriform plate and a voltage is applied, an electric field traversing the posterior portion of the prefrontal cortex is created. Accordingly, this embodiment allows specific removal of anionic aluminum complexes within the posterior portion of the prefrontal cortex.

The cathode may be made from any conventional conductive material used in biomedical applications, including silver and copper.

Figure 5:
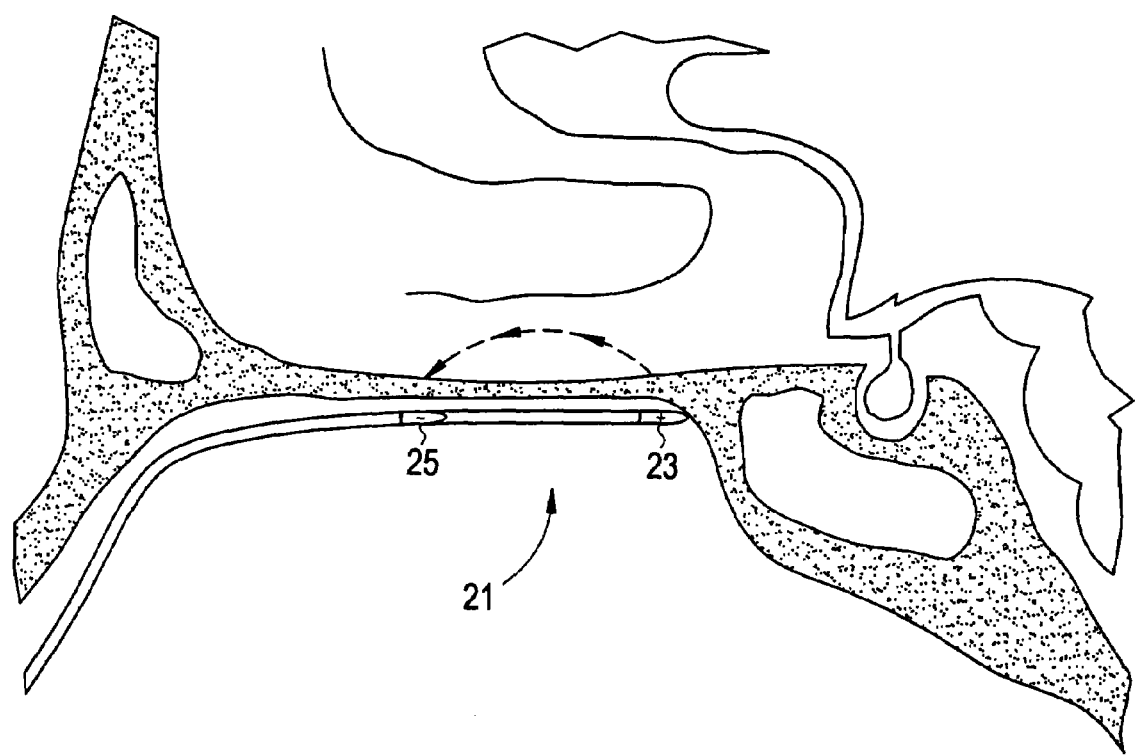

In other embodiment, the invention comprises a bipolar probe having both an anode and a cathode. Now referring to FIG. 5, in some embodiments thereof, the cathode is placed at the proximal end of the probe so that it rests against the anterior wall of the sphenoidal sinus within the nasal cavity. The resulting electric field may extend about 2 cm into the prefrontal cortex.

Now referring to back to FIG. 1b, in intranasal probe 21 comprising a distal cathode 23 and a proximal anode 25.

In some embodiments, the devices disclosed in U.S. Pat. No. 6,410,046 "Administering Pharmaceuticals to the Mammalian Central Nervous System" ("Lerner I"); U.S. Pat. No. 6,678,553, "Device for Enhanced Delivery of Biologically Active Substances and Compounds in an organism" ("Lerner II"); US Published Patent Application No. US 2002/0183683 "Methods and Apparatus For Enhanced and Controlled Delivery of a Biologically Active Agent into the Central Nervous System of a Mammal" ("Lerner IV"), and Lerner, *J. Drug Testing*, June 2004, 12(5) 273-280 ("Lerner V"), the specifications of which are incorporated by reference in their entireties, are selected as the cathodes, anodes and power sources.

The voltage applied across the electrodes should be sufficient to create the desired electric field capable of driving anionic aluminum complexes from the AD brain, but not so great as to cause damage to the brain or other tissue. In particular, the applied voltage should not be so great as to damage the olfactory bulb that lies adjacent the anode. In preferred embodiments, the applied voltage is sufficient to produce a current of between about 1 mA and about 20 mA. More preferably, the current produced thereby is less than about 10 mA.

In some embodiments, hypertonic saline is applied to the nasal mucosa. This has the effect of increasingly the conductivity of the tissue surrounding the anode. In some embodiments, hypertonic saline is applied through the cribriform plate into the CSF. This has the effect of increasingly the conductivity of the local CSF and ECF.

In some embodiments, a periodic voltage is applied so that the olfactory bulb is therapeutically depolarized. When depolarized, the olfactory bulb releases neurotrophic factors to the horizontal limb of the BB. These neurotrophic factors provide support to various portions of the limbic system and prefrontal cortex.

In some embodiments, a device having an anode, an antenna and a cathode are implanted into the brain. The device may be energized by transdermal application of Rf energy to the antenna. The current resulting therefrom produces a positive charge at the anode, thereby preferentially drawing anionic aluminum complexes to the anode. The current resulting therefrom produces a negative charge at the cathode, thereby preferentially drawing cationic metals to the cathode, where they are plated upon the cathode. In some embodiments, the cathode is made of titanium or platinum.

In other embodiments, a galvanic battery containing dissimilar metals is employed. The galvanic battery produces a current, which produces a negative charge at the cathode, thereby preferentially drawing cationic metals to the cathode, where they are plated upon the cathode. In preferred embodiment, the cathode comprises platinum and the anode comprises magnesium.

In some embodiments, a portion of the patient's CSF is withdrawn and sampled in order to determine whether the patient's CSF possesses sufficiently high levels of aluminum (or other charged species) to warrant the therapy of the present invention.

Although the above description relates specifically to the removal anionic aluminum species from the brain, it is believed that similar concepts can be applied to other charged species, such as heavy metals such as copper, iron and zinc. Each of these metals has been implicated in assisting in the oligomerization of soluble beta amyloid.

In some embodiments, cationic copper species are removed. Finefrock, *J. Am. Geriatr. Soc.*, 51, 1143-1148, (2003) reports that there is evidence for the generation of hydrogen peroxide via a beta amyloid-copper complex as a mechanism of beta-amyloid mediated neurotoxicity.

Figure 6:
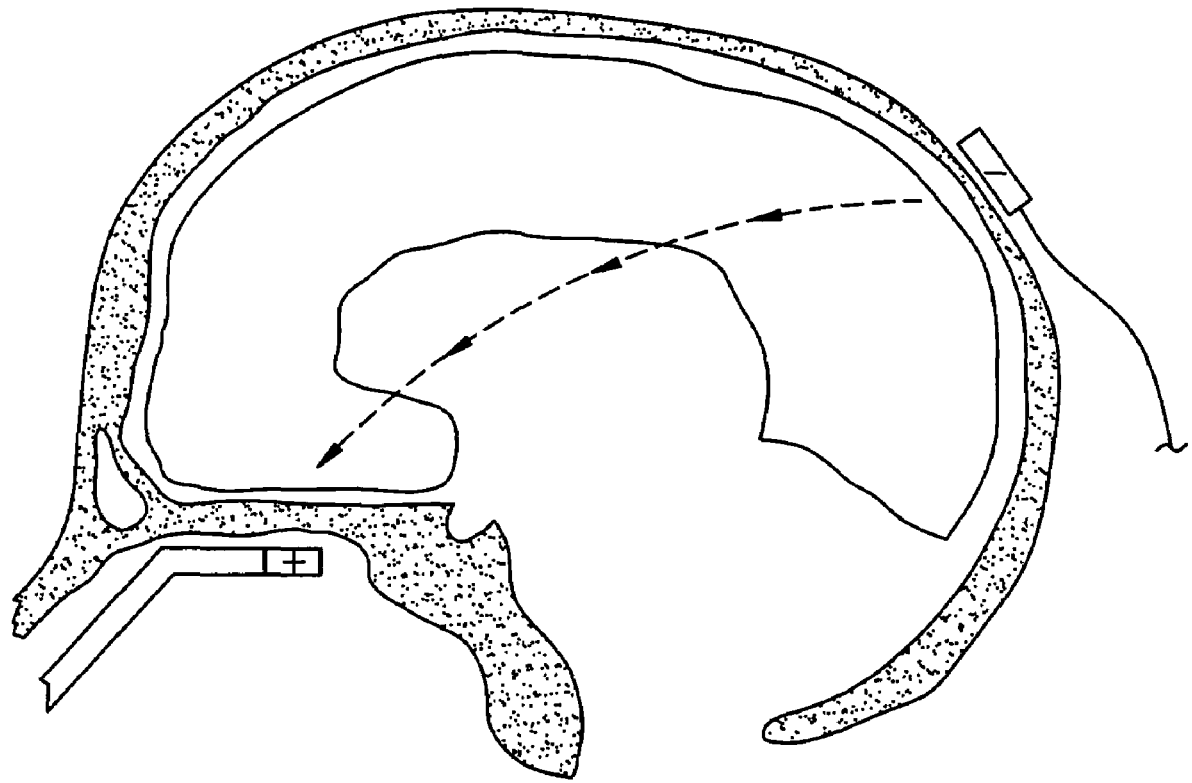
FIG. 6 is a saggital cross-section of a skull having an intranasal cathode and an anode placed on the back of the skull.

In the brain, copper is present substantially in the cationic form. Since this is a positive species, it is believed that providing a cathode at the cribriform plate will draw those species through the cribriform plate, as in FIG. 6.

In some embodiments, the patient has a copper (+2) concentration in the CSF of at least 1 μM. In some embodiments, the patient has a copper (+2) concentration in the CSF of at least 10 μM.

In the brain, iron is present substantially in the cationic form. Since this is a positive species, it is believed that providing a cathode at the cribriform plate will draw those species through the cribriform plate.

It has been reported that zinc may serve a twin role by both initiating amyloid deposition and then being involved in mechanisms attempting to quench oxidative stress and neurotoxicity derived from the amyloid mass. Huang, *J. Nutrition,* 2000, May 130 (5S Supp.) 1488S-92S, and Finefrock, *J. Am. Geriatr. Soc.,* 51, 1143-1148, (2003)

In the brain, zinc is present in the cationic form. Since this is a positive species, it is believed that providing a cathode at the cribriform plate will draw those species through the cribriform plate.

Because the handheld device of the present invention is non-invasive, it is possible to repeatedly perform the procedure of the present invention. In some embodiments, the present invention is carried out at least once a month. In some embodiments, the present invention is carried out at least once a week. In some embodiments, the present invention is carried out substantially daily.

Stroke

According to Mancia, *Clin. Ther.* 2004, May 26(5), 631-48, each year, stroke occurs in 30.9 million individuals worldwide and is responsible for approximately 4 million deaths. In the United States, it is the third leading cause of death, occurring with greater frequency than myocardial infarction in patients with hypertension. The greatest burden of stroke, apart from death, is serious long-term physical and mental disability. Stroke survivors often experience physical handicap, depression, and cognitive dysfunction, which together affect their daily functioning, quality of life, and survival. The treatment of stroke is associated with extremely high costs, with stroke-related illnesses responsible for more than $49 billion in the United States in 2002.

It is now known that stroke pathology is not a singular event, but rather a succession of events that cause progressive damage. At the onset of a stroke, occluded blood flow to the brain leads to lower levels of oxygen and glucose in the nearby cells. Because neurons rely upon glucose and oxygen to produce energy through phosphorylation, these affected neurons become prone to energy failure. This energy failure produces a periodic depolarization of this region, thereby releasing very large amounts of glutamate (an important synaptic neurotransmitter) from the dying cells into the extracellular fluid. The amount of glutamate so released is so large that typical glutamate transporter processes become overwhelmed, thereby causing glutamate to persist too long in the ECF. This persistence in the ECF forces ion gates and channels to remain open, thereby providing an opportunity for an excessive in rush of calcium ions. These calcium ions cause the overproduction of neuron degrading enzymes, leading to infarction.

Although the brain cells within the infarcted region are lost, it is now known that the brain cells in the adjacent regions of the brain ("the penumbra") may still be saved. Within hours of the stroke onset, inflammation invades the penumbra, exposing the penumbra to more neurotoxic agents such as TNF-α and Il-1β. Accordingly, modern stroke therapy has focused upon saving the brain cells in the penumbral region from these neurotoxic agents.

Many investigators have focused upon inhibiting the glutamate receptors. This approach attempts to inhibit the binding of glutamate to its synaptic receptor, and thereby reduce the permeability of the ion gates to calcium inrush. Although these attempts have been shown to be successful in laboratory experiments, one of the problems associated with glutamate receptor inhibition is that these therapeutic molecules inhibit not only the receptors in the infarcted regions, but also the glutamate receptors in the penumbral regions and otherwise healthy regions of the brain, thereby causing undesirable side effects that affect normal synaptic transmission.

The present inventors believe that excessive levels of glutamate in the ECF of an infarcted region and penumbra of a stroke patient can be reduced by applying reverse iontophoresis. Because glutamate has a low molecular weight (<100 MW) and is stable in a anionic state in the brain ECF, it is likely a highly mobile species when brought under the influence of an electric field. The present inventors believe that the electric field can be therapeutically applied to the affected region to draw glutamate out of the ECF compartment of the infarcted and penumbral regions, through the cerebrospinal fluid (CSF) and out of the cranium, whereby it can be safely released into the lymphatic system.

Because the removal of significant amounts of glutamate from this compartment will return a balance to the glutamate—receptor equilibrium and thereby restore ion gate permeability to desirable levels in the penumbral region, the penumbral region will be spared of significant amounts of cytotoxic inflammation.

Moreover, since application of the electric field will likely drive the movement of only extracellular glutamate, but not intracellular glutamate, this therapy will avoid the complete abolition of the desired physiologic function of glutamate and so will not have the undesired side effects brought on by glutamate receptor inhibitors.

Lastly, because the therapy focuses upon the removal of an excessive component which has been released from dying cells, it is believed that a single application of the electric field will be sufficient to remove the excessive glutamate. Moreover, there will be little if any undesired after-effect of the therapy once the therapy has been completed.

Therefore, in accordance with the present invention, there is provided a method of treating a stroke patient having an infarcted region, comprising the steps of:

a) passing an electric field through the infarcted region in an amount effective remove glutamate from the infarcted region.

Preferably, the reverse iontophoresis is applied to the stroke patient within the first 24 hours of stroke onset. More preferably, it is applied to the stroke patient within the first 6 hours of stroke onset, most preferably, it is applied to the stroke patient within the first hour of stroke onset.

Because glutamate has such a low molecular weight, it is believed that it will be readily removed from the infarcted and penumbral regions upon application of the electric field. Accordingly, in some embodiments, the electric field is applied to the infarcted and penumbral regions for a period of no more than one hour, preferably less than 30 minutes, more preferably less than 10 minutes.

Figure 7:
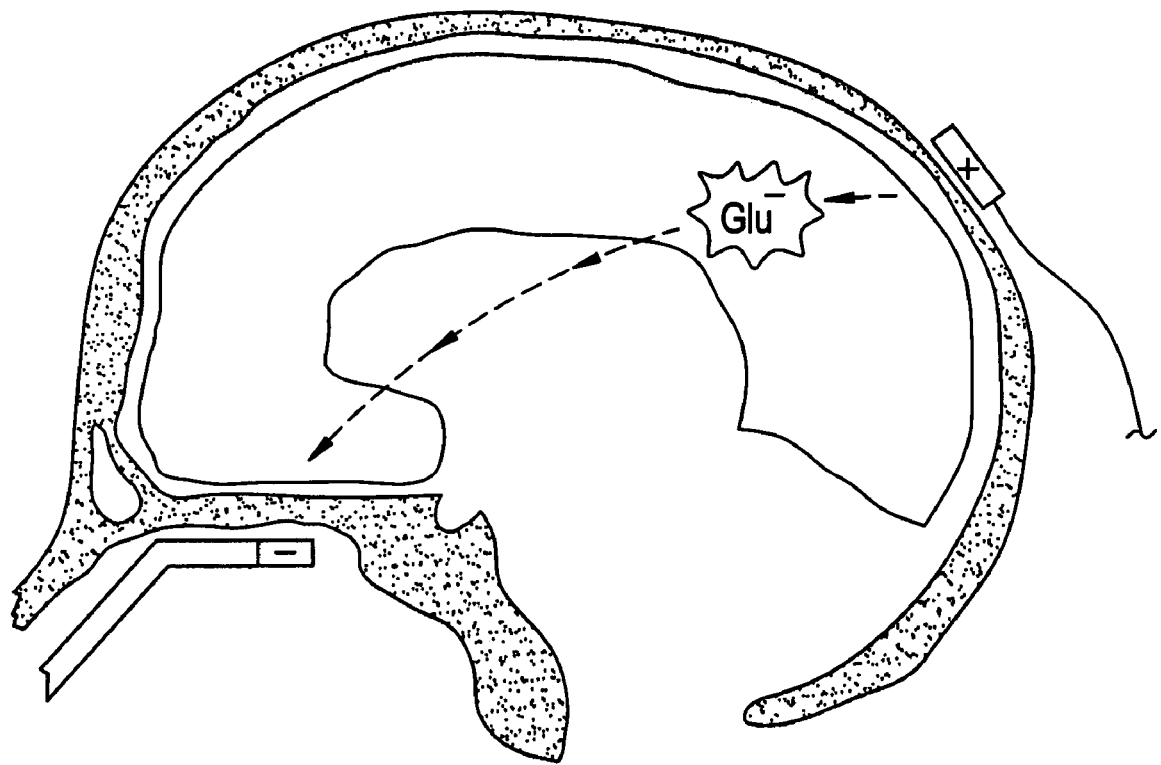
FIG. 7 is a saggital cross-section of a cerebrum having an occipital infarct, wherein the device of the present invention comprises an intranasal anode and a cathode placed on the back of the skull.

If the location of the infarct is not known, then it may be useful to provide an electric field over as large a volume of the cerebrum as possible. Therefore, in some embodiments, and now referring to FIG. 7, the anode (−) and cathode (+) are placed at opposite ends of the skull. In this FIG. 7, the anode is placed against the cribriform plate while the cathode is placed on the back of the skull. Anionic glutamate present within the infarct and penumbral regions ($Glu^-$) is drawn anteriorly across the brain to be drained out through the cribriform plate.

It has been estimated that about 25% of strokes occur in the frontal lobe of the brain. Therefore, in preferred embodiments related to stroke management, an electric field is passed through the infarcted and penumbral regions located in the frontal lobe ($Glu^-$) in an amount effective remove glutamate from the infarcted and penumbral regions.

Figure 8:
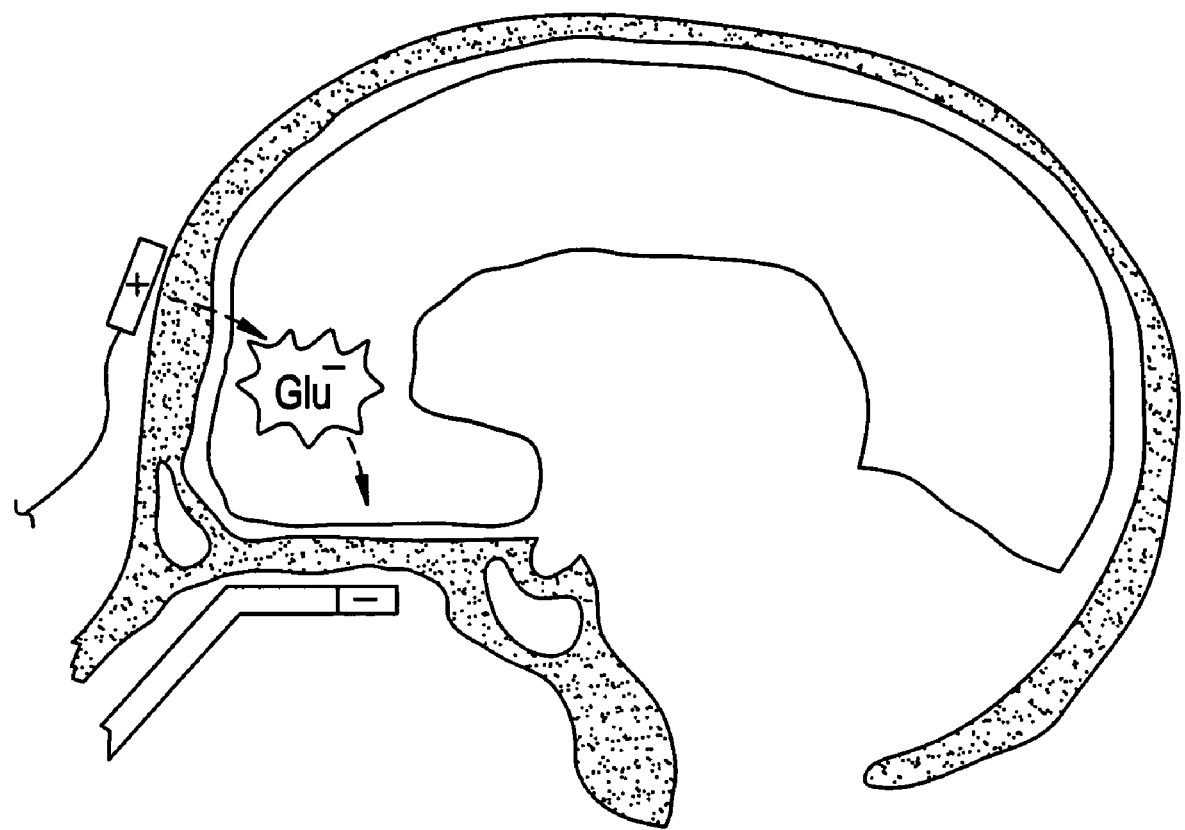
FIG. 8 is a saggital cross-section of a cerebrum having a frontal infarct, wherein the device of the present invention comprises an intranasal anode and a cathode placed on the forehead.

Now referring to FIG. 8, in preferred embodiments thereof, a cathode may be placed on the forehead of the patient and the anode may be inserted intranasally so that it abuts the cribriform plate. Application of voltage to the electrodes will result in an electric field as shown in FIG. 8 that passes through the infarcted and penumbral regions of the frontal lobe. This field will cause the charged glutamate molecules within these regions ($Glu^-$) to move towards the anode and into the CSF located just above the cribriform plate. The glutamate will then pass through the cribriform plate and into the lymphatic drainage system located in the nasal mucosa.

In preferred embodiments, the cathode placed on the forehead is provided in the form of a plate in order to maximize the volume of the frontal lobe that will be under the influence of the electric field and therefore therapeutically treated. Preferably, the plate contour corresponds substantially to the contour of a human forehead.

Some portion of strokes occur in the occipital lobe portion of the brain. Therefore, in preferred embodiments related to stroke management, an electric field is passed through the infarcted and penumbral regions located in the occipital lobe in an amount effective remove glutamate from the infarcted and penumbral regions.

Figure 9:
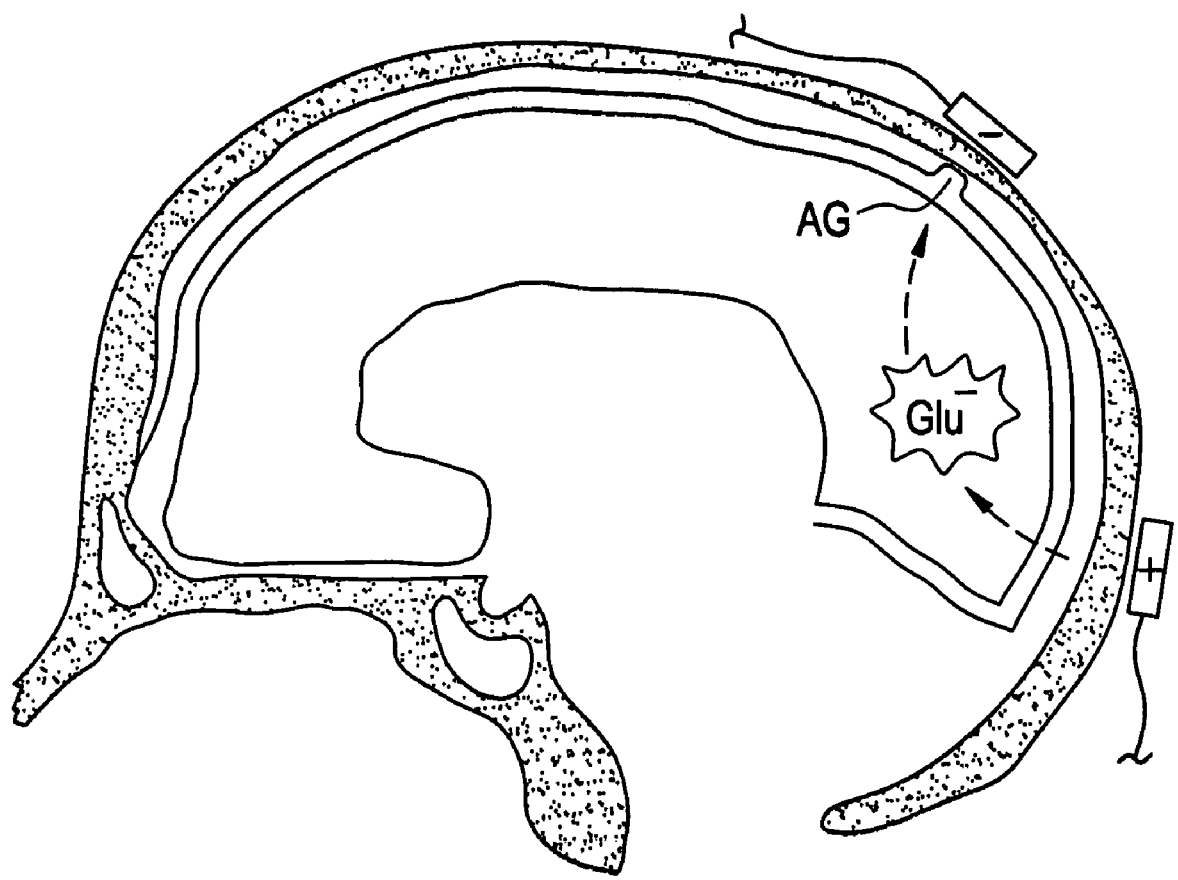
FIG. 9 is a saggital cross-section of a cerebrum having an occipital infarct, wherein the device of the present invention comprises an anode located adjacent an arachnoid granulation and a cathode placed on the back of the skull.

Now referring to FIG. 9, in preferred embodiments thereof, a cathode of the occipital embodiment may be placed on a first portion of the back of the skull and the anode may be placed on a second portion of the back of the skull located adjacent an arachnoid granulation AG. Application of a voltage to the electrodes will result in an electric field as shown in FIG. 9 that passes through the infarcted and penumbral regions ($Glu^-$) in the occipital lobe. This field will cause the charged glutamate molecules within these regions to move towards the anode located adjacent an arachnoid granulation. Because the arachnoid granulation can be considered to be a sink for CSF, the glutamate molecules flowing thereto will flow from the CSF in the subarachnoid space and into the venous system. The glutamate will then pass into the lymphatic drainage system located in this region.

In preferred embodiments, the anode and cathode placed on the occipital lobe are provided in the form of plates in order to maximize the volume of the occipital lobe that will be under the influence of the electric field. Preferably, the plate contours correspond substantially to the contour of the back of a human skull.

Figure 10:
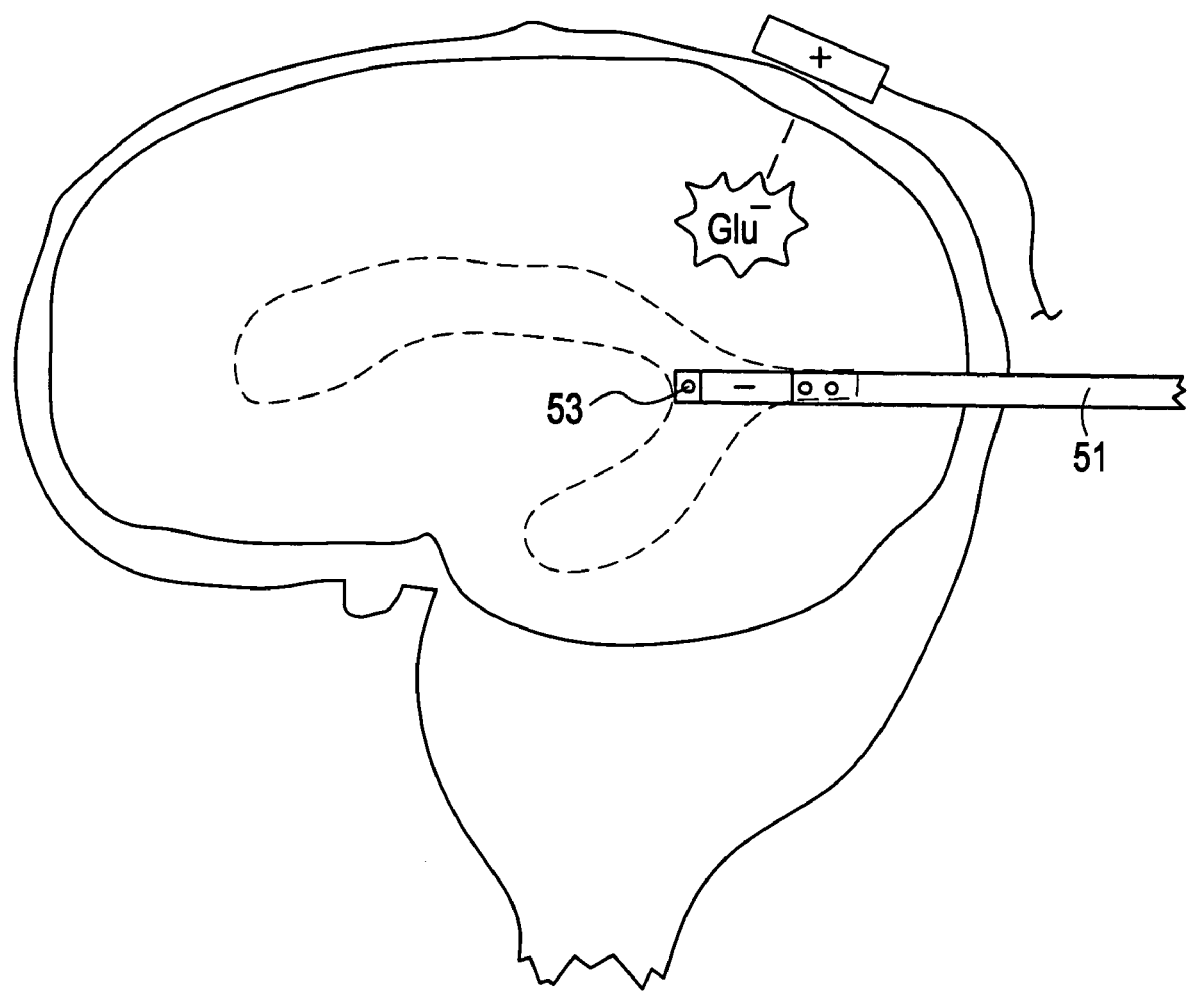
FIG. 10 is a saggital cross-section of a cerebrum having an occipital infarct, wherein the device of the present invention comprises an intraventricular anode and a cathode placed on the back of the skull.

Now referring to FIG. 10, in preferred embodiments of treating occipital infarcts, a cathode may be placed on a first portion of the back of the skull and the anode may be placed within a ventricle of the brain (shown as a dotted line region). Ventricular placement is attractive because it allows the surgeon to place the anode deep within the brain with a minimum of disruption to neurological tissue. Application of current to the electrodes will result in an electric field as shown in FIG. 10 that passes through the infarcted region ($Glu^-$) of the cerebrum. This field will cause the charged glutamate molecules within this region to move towards the anode located in the ventricle. The probe 51 containing the anode also comprises a cannula having holes 53 at the distal end thereof for drawing in CSF by activation of a vacuum source (not shown) connected to the cannula. The glutamate will then pass into the ventricle and drain through the holes located in a cannulated portion of the anodic probe.

Figure 11:
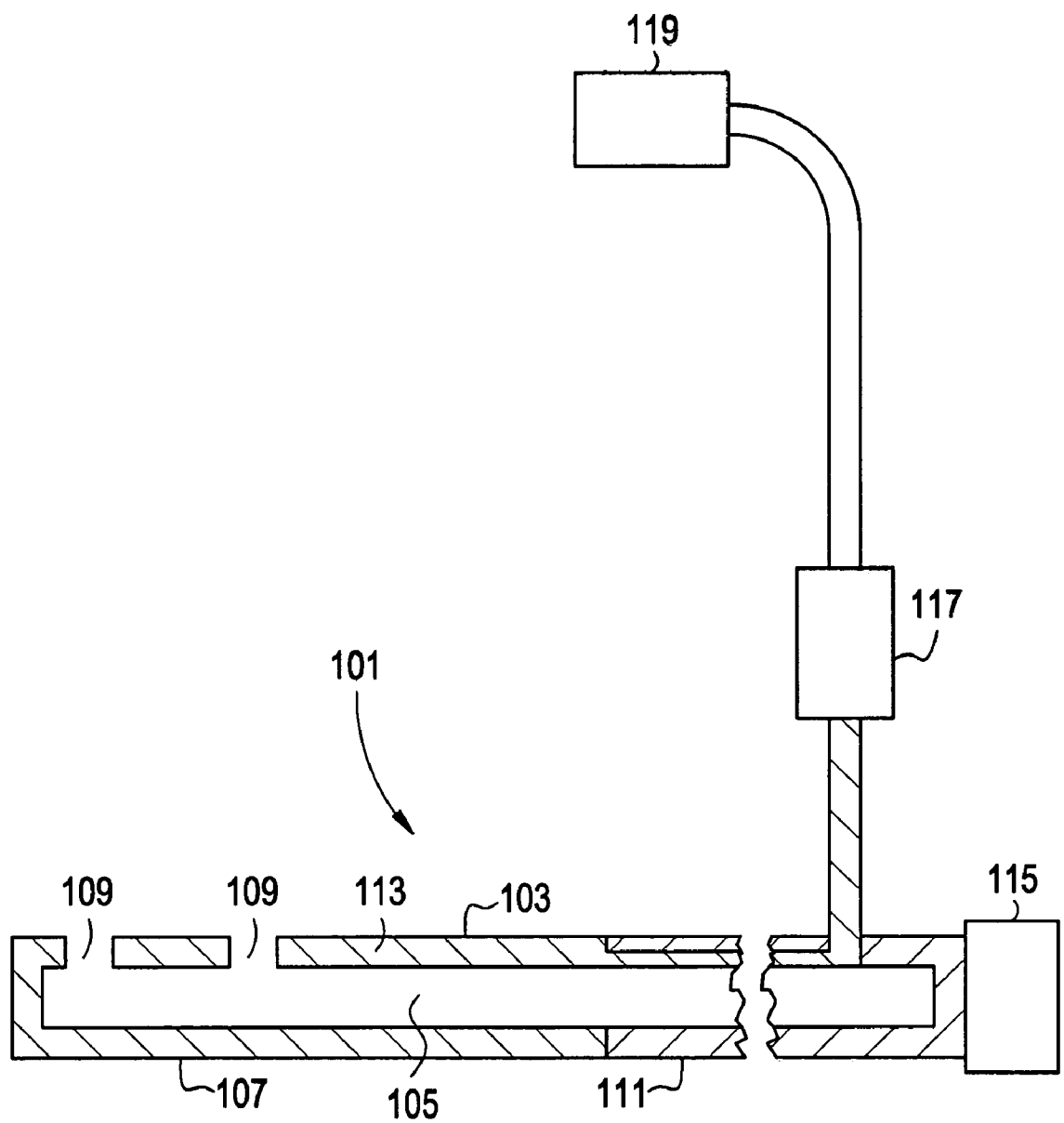
FIG. 11 is a cross section of an anodic probe of the present invention.

Therefore, and now referring to FIG. 11, in accordance with the present invention, there is provided a system for removing charged species from brain tissue, comprising:

a) a probe 101 adapted for placement within brain tissue, the probe having a distal cannula 103 having an inner bore 105 and an outer surface 107, a plurality of holes 109 communicating with the inner bore and the outer surface, a proximal insulating portion 111 and a distal electrode portion 113, and b) a vacuum source 115 in fluid connection with the inner bore, c) a cathode 119 adapted to be located on the skull of the patient, and d) a voltage source 117 in electrical connection with the anode and cathode.

Figure 12:
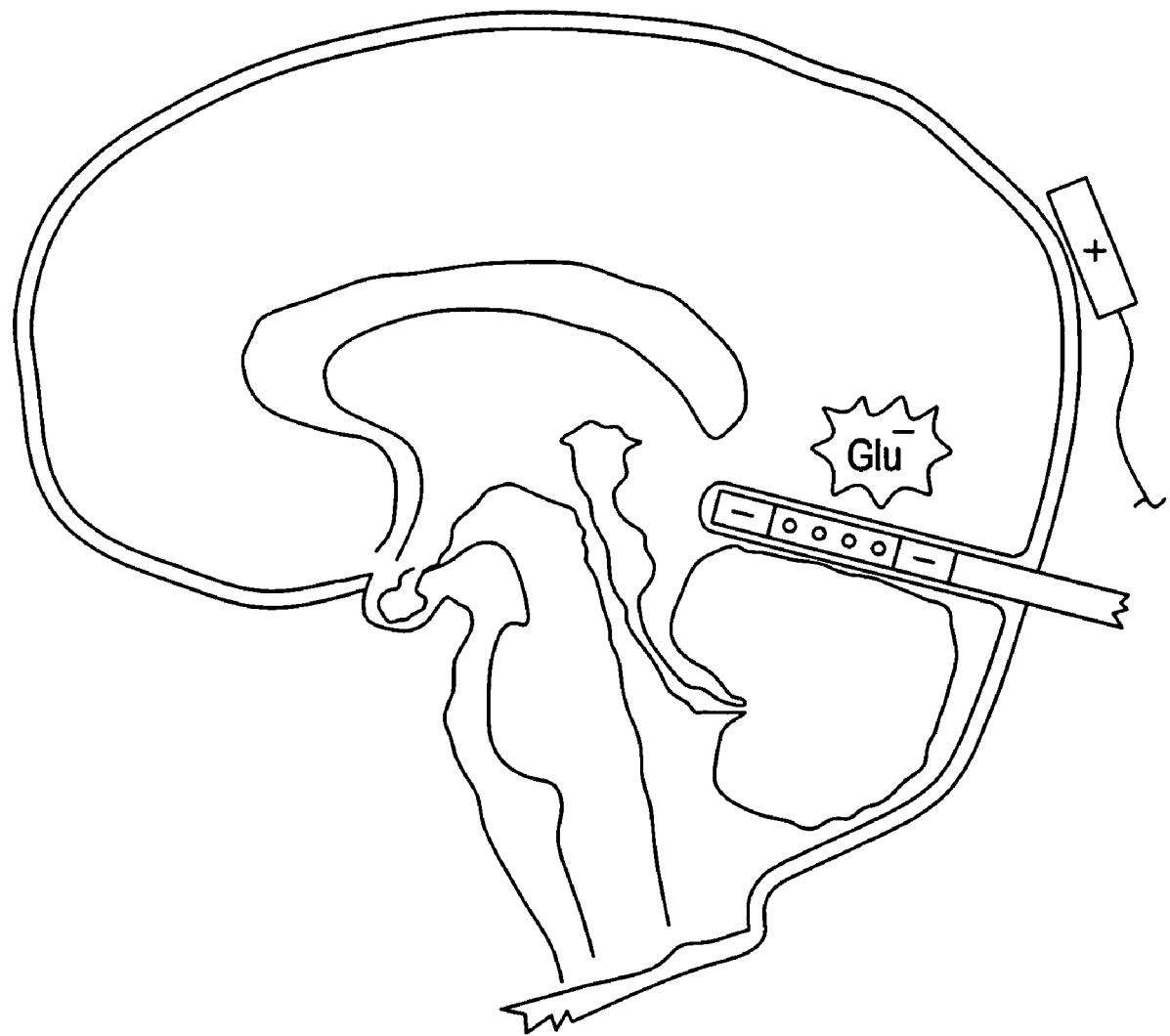
FIG. 12 is a saggital cross-section of a cerebrum having an occipital infarct, wherein the device of the present invention comprises an anode adjacent the straight sinus and a cathode placed on the back of the skull.

Now referring to FIG. 12, in preferred embodiments thereof, a cathode may be placed on a first portion of the back of the skull and the anodic probe described above may be placed adjacent to the straight sinus of the brain. Placement of the anodic probe next to the straight sinus is attractive because it allows the surgeon to place the anode at any depth directly adjacent the occipital portion of deep the brain without invading brain tissue. Application of current to the electrodes will result in an electric field that passes through the infarcted region ($Glu^-$) of the cerebrum. This field will cause the charged glutamate molecules within this region to move towards the anode located adjacent the straight sinus. The probe containing the anode comprises a cannula having holes at the distal end thereof for drawing in CSF by activation of a vacuum source (not shown) connected to the cannula. The glutamate will then pass into the cannula and drain through the holes located in a cannulated portion of the anodic probe.

Because it would be helpful to precisely the location of the infarct in order to insure that the electric field will be passed therethrough, in some embodiments, a diagnostic procedure that identifies the precise location of the infarct is carried out prior to application of the electric field. In some embodiments, the diagnostic procedure is an MRI. In some embodiments, the diagnostic procedure is a CAT scan.

In some embodiments, the electric field is applied with a strength and for a duration sufficient to reduce the peak concentration of glutamate in the infarcted region by at least 10%. Preferably, the electric field is applied with a strength and for a duration sufficient to reduce the peak concentration of glutamate in the infarcted region by at least 30%, more preferably at least 50%, more preferably at least 75%.

I claim:

1. A method of treating a stroke patient having an infarcted region located in an occipital lobe and a skull having a back, comprising the steps of:

a) placing a cathode on a first portion of the back of the skull, b) placing an anode on a second portion of the back of the skull located adjacent an arachnoid granulation, and c) applying a voltage between the anode and cathode to pass an electric field through the infarcted region located in the occipital lobe in an amount effective remove glutamate from the region, and d) drawing glutamate out of the infarcted region due to the application of the voltage, wherein the infarcted region contains an excessive level of glutamate in an extracellular fluid that is effective to overwhelm glutamate transporter processes, thereby causing glutamate to persist too long in the extracellular fluid and force ion gates and channels to remain open, thereby providing an excessive in rush of calcium ions which cause overproduction of neuron degrading enzymes, leading to the infarction.

2. The method of claim 1 wherein a diagnostic procedure that identifies a location of the infarct is carried out prior to application of the electric field.

3. The method of claim 2 wherein the diagnostic procedure is an MRI.

4. The method of claim 2 wherein the diagnostic procedure is a CAT scan.

5. The method of claim 1 wherein the electric field is produced by a current having a strength of no more than about 20 mA.

6. The method of claim 1 wherein the electric field is applied to the stroke patient within the first 24 hours of stroke onset.

7. The method of claim 1 wherein the electric field is applied to the stroke patient within the first 6 hours of stroke onset.

8. The method of claim 1 wherein the electric field is applied to the infarcted region for a period of no more than one hour.

9. The method of claim 1 wherein the electric field is applied to the infarcted region for a period of less than 30 minutes.

* * * * *